US011291582B2

(12) United States Patent
van de Graaf et al.

(10) Patent No.: US 11,291,582 B2
(45) Date of Patent: Apr. 5, 2022

(54) SYSTEM FOR REVERSIBLE CONTRACEPTIVE STERILIZATION (71) Applicant: Choice B.V., Sevenum (NL)

(72) Inventors: Peter van de Graaf, Sevenum (NL); Erwin Dekkers, Sevenum (NL)

(73) Assignee: CHOICE B.V., Sevenum (NL)

( * ) Notice: Subject to any disclaimer, the term of this patent is extended or adjusted under 35 U.S.C. 154(b) by 756 days.

(21) Appl. No.: 15/508,578

(22) PCT Filed: Sep. 4, 2015

(86) PCT No.: PCT/NL2015/050614
§ 371 (c)(1),
(2) Date: Mar. 3, 2017

(87) PCT Pub. No.: WO2016/036248
PCT Pub. Date: Mar. 10, 2016

(65) Prior Publication Data
US 2017/0281401 A1 Oct. 5, 2017

(30) Foreign Application Priority Data
Sep. 5, 2014 (NL) ...................................... 2013424

(51) Int. Cl.
A61F 6/24 (2006.01)
(52) U.S. Cl.
CPC ...................................... *A61F 6/24* (2013.01)
(58) Field of Classification Search
CPC ...... A61F 6/24; A61F 6/20; A61F 2/82; A61F 2/2412; A61F 2/2475; A61F 5/4405;
(Continued)

(56) References Cited

U.S. PATENT DOCUMENTS 3,777,737 A 12/1973 Bucalo
8,616,212 B1 * 12/2013 Logan .................. A61M 39/22
128/831
2011/0067705 A1 3/2011 Kennedy

FOREIGN PATENT DOCUMENTS

JP 02241990 9/1990
JP H02 241990 A * 9/1990
(Continued)

OTHER PUBLICATIONS

European Patent Office, International Search Report in co-pending International Application No. PCT/NL2015/050614 dated Dec. 23, 2015 (5 pages).

Primary Examiner — Caitlin A Carreiro
(74) Attorney, Agent, or Firm — Leydig, Voit & Mayer, Ltd.

(57) ABSTRACT

A system for reversible contraceptive sterilization is described. It is proposed to provide an implantable tube valve for implanting in a human vessel, in particular, the fallopian tube. The implantable tube valve includes: an implantable tube having an inner tube wall extending between two axial tube ends and includes a mount inside the tube; and a valve member mounted in the mount and pivotable between an open position and a closed position. The valve member includes a sealing edge that contacts the inner tube wall, when pivoted in the closed position, with the valve member closing off passage through the implantable tube. The valve member further includes an outer face conformal to the inner tube wall and an inner face conformal to the outer face, thereby providing unobstructed passage through the implantable tube when pivoted in the open position.

12 Claims, 7 Drawing Sheets (58) Field of Classification Search
CPC ...... A61F 5/441; A61F 2/0009; A61F 2/0004;
A61F 2/0022; A61F 2/24; A61F 2/2476;
A61F 2/2403; A61F 2/2424; A61F 2/04;
A61F 6/06; A61F 6/00; A61F 6/02; A61F
6/146; A61M 2205/04; A61M 2210/14;
A61M 2210/16; A61M 39/22; Y10S
623/90; A61B 8/445; A61B 17/0057;
A61B 17/12022; A61B 17/12099; A61B
17/12109; A61B 17/12122; F16K 25/00;
F16K 21/00; F16K 51/00; F16K 15/182;
F16K 15/184
USPC ........ 128/831, 843, 830, 842, 887; 600/467,
600/29–32, 466; 606/193, 194;
623/1.15, 1.24, 1.26, 1.1, 2.1, 2.2, 23.64,
623/23.68; 137/247, 247.13, 247.19,
137/247.21, 251.1
See application file for complete search history.

(56) References Cited

FOREIGN PATENT DOCUMENTS

WO     WO 2013/144770 A2    10/2013
WO     WO-2013144770 A2 *   10/2013    ......... A61F 2/0022

* cited by examiner

SYSTEM FOR REVERSIBLE CONTRACEPTIVE STERILIZATION

CROSS-REFERENCE TO RELATED APPLICATIONS

This patent application is a U.S. National Phase of PCT International Application No. PCT/NL2015/050614, filed Sep. 4, 2015, which claims priority to Netherlands Application No. 2013424, filed Sep. 5, 2014, the contents of which are expressly incorporated herein by reference in there entireties, including any references therein.

FIELD OF INVENTION

The invention relates to a system for reversible contraceptive sterilization in a human body.

DESCRIPTION OF THE PRIOR ART

With the dawn of modern implant technology several attempts were made to provide the human reproductive system with a means for being able to decide whether one chooses to be fertile or not. For example, switching arrangements, such as tube implants in prior art designs for insertion into the female organ, aim to ensure an anti conceptive function, for example of the type disclosed in U.S. Pat. No. 5,935,137. None of these however, offer a reliable and efficient solution for protection that can be switched on and off at will. A problem with these devices is the miniature dimensions of insertion in the reproductive system, in particular, the fallopian tube, which typically has a diameter of less than 3 mm.

For these dimensions it is difficult to propose a solution, that matches a desire of continuous and reliable use, that can be operated without a need for medical adjustment over a prolonged period of time.

SUMMARY OF THE INVENTION

In one aspect, it is aimed to provide an implantable tube of the type that can be implanted in a human vessel, in particular, the fallopian tube, that functions autonomously without further need for medical intervention, and that can be operated by a simple remote device. To this end it is proposed to provide an implantable tube valve for implanting in a human vessel, in particular, the fallopian tube that comprises an implantable tube having an inner tube wall extending between two axial tube ends; and a valve member mounted inside said tube wall. The valve member is pivotable between an open position and a closed position and comprises a sealing edge contacting the inner tube wall, when pivoted in the closed position. Thereby the valve member closes off passage through the implantable tube. The valve member further comprises an outer face extending from the sealing edge conformal to the inner tube wall; and an inner face extending from the sealing edge conformal to the outer face thereby providing unobstructed passage through the implantable tube, when pivoted in the open position. Similarly, the device may be implanted in other tubes or vessels such as the vas deferens, bowels or urinary ducts, for example to counter incontinency problems.

Another aspect of the invention concerns an actuator comprising a mounting structure and an actuating member pivotable relative to the mounting structure, the mounting structure having an axis of elongation further comprising a heating circuit and first and second tension wires aligned along the axis of elongation, the tension wires formed of a shape metal alloy, connected to the heating circuit and eccentrically engaging the actuating member thereby pivoting the actuating member to positions relative to the mounting structure, so that, in use, the actuating member is pivoted in a first position by heating the first tension wire and the actuating member is pivoted in a second position by heating the second tension wire.

The actuator is very suitable for use where only compact, in particular flat, elongated space constraints are present. In this particular embodiment it may act as an actuator on the side of a tube, whereby the actuator does not add significantly to the diameter of the tube Another aspect of the invention concerns a system of a wireless charging device and an implantable tube device as herein disclosed.

BRIEF DESCRIPTION OF THE DRAWINGS

The invention will be further elucidated in the figures.

and

DETAILED DESCRIPTION

Unless otherwise defined, all terms (including technical and scientific terms) used herein have the same meaning as commonly understood by one of ordinary skill in the art to which this disclosure belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be further understood that the terms "comprises" and/or "comprising" specify the presence of stated features but do not preclude the presence or addition of one or more other features. All publications, patent applications, patents, and other references mentioned herein are incorporated by reference in their entirety. In case of conflict, the present specification, including definitions, will control.

The term "mount" is used in its ordinary meaning to emphasize that many mounting arrangements are possible. These arrangements include physical shaft mounts, ball bearing mounts or any other mechanical arrangement providing a rotational degree of freedom for the valve member mounted in the mount. The rotational degree of freedom defines an axis of rotation or pivot axis that is transverse to the implantable tube. Preferably, the mount is formed partly by the tube, and a corresponding mount part formed by the valve member.

The term "conformal to" is used in its ordinary meaning to indicate the form following nature of the identified features, meaning that shape and size are similar for a substantial part of said features. In mathematical sense the meaning conformal indicates that the features preserve shape on a local scale. To illustrate that some deviation may be allowed, depending on the specifics of the application it is considered that certain features, e.g. a valve member's outer and inner face are considered conformal if a thickness between the two varies with e.g. less than 10%.

In stricter sense, it is considered that 'contiguous to' means that the form is not only similar, but identical so that there virtually no or only a very small gap between the two features, e.g. less than 0.1 mm, in particular less than a diameter of a human egg cell. In a more abstract sense, the term 'coincides with' is used to indicate that a feature is enveloped by a notional feature coinciding with an outer face over a substantial part of said feature.

By the term 'extending continuously' e.g. between axial tube ends, it is indicated that there are no substantial deviations present between said extensions, notably no or very limited protruding outer features, in respect of the implantable tube. In particular, the implantable tube extending continuously between the axial tube ends indicates that there is no or very limited spatial deviation from the tube form along the entire tube. The term continuous does nevertheless not preclude the presence of minor protrusions or depressions, e.g. for forming an actuator housing, sealing edge, mounting or valve seat on a smaller scale or for forming a rugged surface e.g. for fixed insertion in the human vessel, e.g. in the form known for stents. It is indicated on a larger scale that the general flow through the object may be unobstructed due to the tube's continuous form, or that the object itself does not substantially deviate from a tube form. In particular, depending on its application, the actuator actuating the valve member is shaped in elongated form along the tube in a way that can be absorbed by stretching the surrounding tissue, e.g. the fallopian tube.

A 'heating circuit' may comprise one or more analog or digital hardwire elements configured to perform operational acts in accordance with the present systems and methods, such as to provide control signals to the various other module components. The processor may be a dedicated processor for performing in accordance with the present system or may be a general-purpose processor wherein only one of many functions operates for performing in accordance with the present system. The processor may operate utilizing a program portion, multiple program segments, or may be a hardware device utilizing a dedicated or multipurpose integrated circuit. Any type of processor may be used such as dedicated or shared one. The processor may include micro-controllers, central processing units (CPUs), digital signal processor s (DSPs), ASICs, or any other processor(s) or controller(s) such as digital optical devices, or analog electrical circuits that perform the same functions, and employ electronic techniques and architecture. The controller or processor may further comprise a memory that may be part of or operationally coupled to the controller. The memory may be any suitable type of memory where data is stored. Any medium known or developed that can store and/or transmit information suitable for use with the present systems and methods may be used as a memory. The memory may also store user preferences and/or application data accessible by the controller for configuring it to perform operational acts in accordance with the present systems and methods.

While example embodiments are shown for systems and methods, also alternative ways may be envisaged by those skilled in the art having the benefit of the present disclosure for achieving a similar function and result. E.g. some components may be combined or split up into one or more alternative components. Finally, these embodiments are intended to be merely illustrative of the present system and should not be construed as limiting the appended claims to any particular embodiment or group of embodiments. Thus, while the present system has been described in particular detail with reference to specific exemplary embodiments thereof, it should also be appreciated that numerous modifications and alternative embodiments may be devised by those having ordinary skill in the art without departing from the scope of the present systems and methods as set forth in the claims that follow. The specification and drawings are accordingly to be regarded in an illustrative manner and are not intended to limit the scope of the appended claims.

Any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage.

Figure 1:
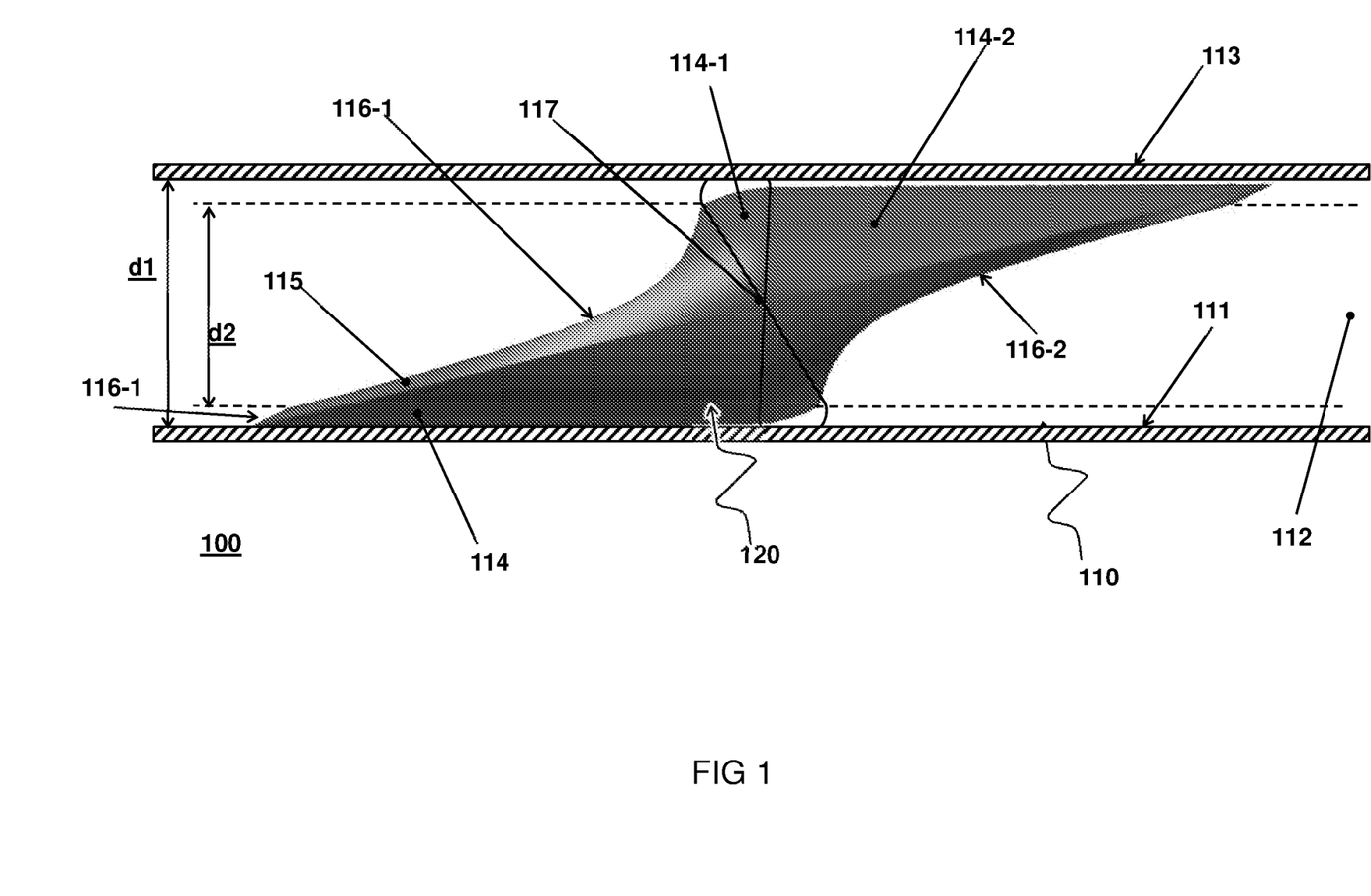
FIG. 1 shows an embodiment of an implantable tube valve device.

Turning now to FIG. 1, there is illustrated an embodiment of an implantable tube valve device 100 according to a first embodiment. The tube valve 110 may be implanted by means of a catheter insertion with means conventional in the art, e.g., depending on application, a catheter for inserting the implantable tube in a designated vessel, in particular, into the fallopian tubes of a female patient, by a catheter inserted through the cervix into the uterus. Similarly, the device may be implanted in other vessels such as the vas deferens, bowels or urinary ducts, for example to counter incontinency problems or any tube transporting fluids or (micro)particles. This is achieved by an implantable tube having an inner tube wall 111 of a diameter d1, e.g. of 2-3 mm, extending between two axial tube ends 112; and a valve member 120 mounted inside said tube 110 and pivotable between an open position and a closed position. The valve device 100 has as a primary advantage its unobstructed flow through the tube when pivoted in open position in an inner diameter d2, e.g. with a diameter of 2-3 mm. In FIG. 1, the valve member 120 is illustrated in an open position. The outer face 114 extends along a beak part 114-1 and a pivot part 114-2 and is conformal to the inner tube wall 111. Inner face 115 is conformal to the outer face 114 thereby providing unobstructed passage through the implantable tube, when pivoted in the open position. The valve member comprises a sealing edge 116 contacting, the inner tube wall when pivoted in the closed position, the valve member 120 thereby closing off passage through the implantable tube 110. For ease of understanding, an actuator for pivoting the valve member 120 between open to the closed position is not shown. In the shown embodiment a mount may be formed by opposite shaft members (not shown) protruding from the valve member through the tube wall thereby forming an axis of rotation, or other suitable mounting arrangements. While a single beak part 114-2 is sufficient, the valve member 120 in depicted form has a second sealing edge 116-2 axially symmetric relative to the first sealing edge 116-1 over pivot 117 having inner and outer faces extending between opposite sealing edges.

Figure 2:
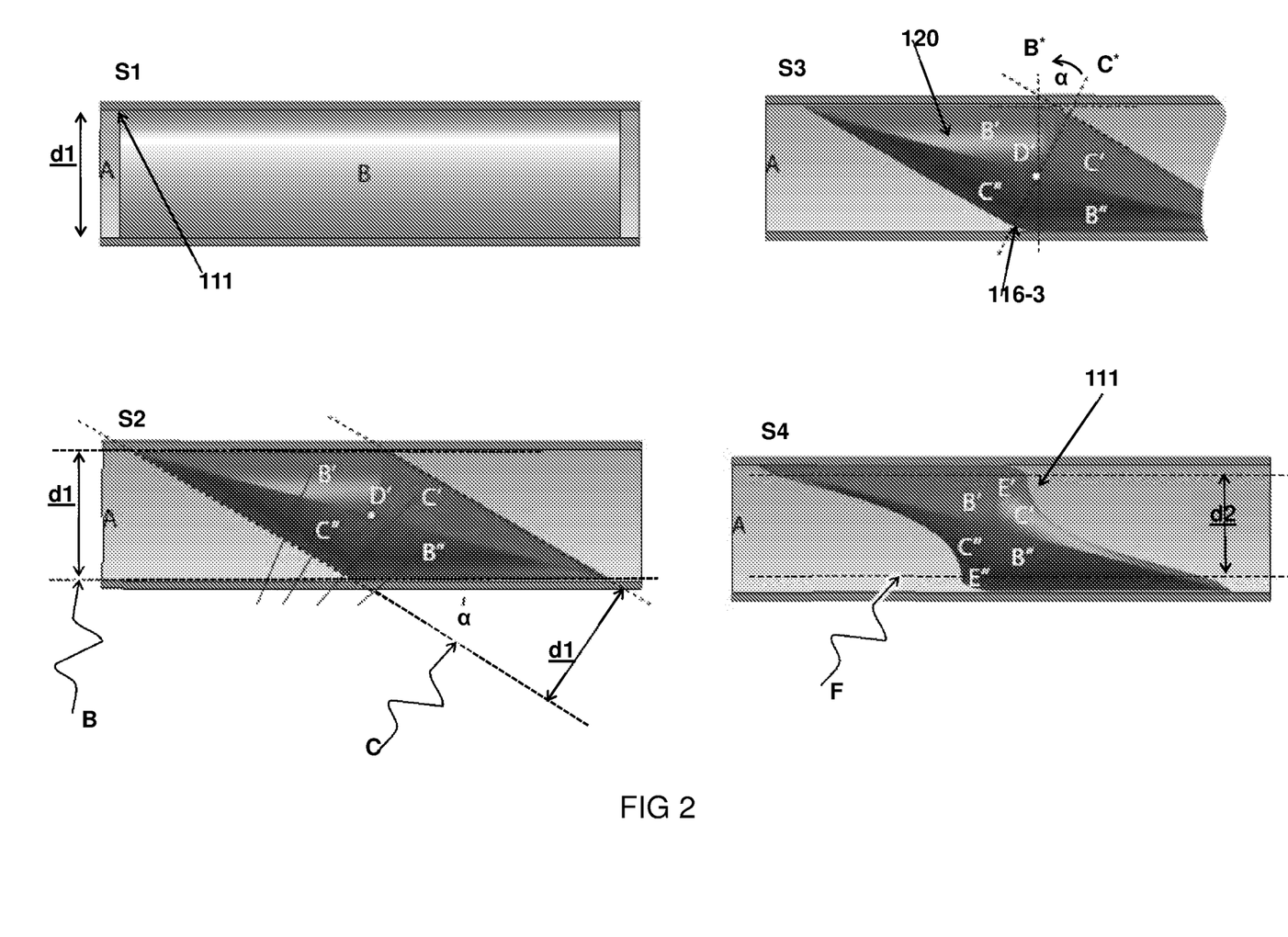
FIG. 2 shows a method of constructing the valve member.

FIG. 2 shows in detail a method of constructing the valve member disclosed in FIG. 1 from known shapes such as cylinders and spheres. In actual construction, for example, the valve member may be formed by machining, moulding or 3D printing techniques.

In a first step S1 one starts with a hollow tube A with inner diameter d1 filled with a first notional body B also with diameter d1. Accordingly a solid inner body is formed as an inner member contiguous to the tube wall 111. In a second step S2 body B is intersected with another notional body C also of diameter d1 under an angle alfa, resulting in a remaining intersection body of cylinders B and C. Valve member, in particular its sealing edge is thus formed by an intersection curve of a first and second notional bodies B and C, the first notional body B coinciding with the inner tube wall A and the second notional body C formed by pivoting the first notional body B over the pivot part D. Body B is thus cut off by an intersecting shape C of the same shape as the hollow inner cylinder but that is angled relative to the longitudinal axis of the tube A. In this way pivot point D' is created on an intersection curve between four segments B', B", C', C" resulting in stable positions within inner tube A. The respective angle alfa between longitudinal axes of tube A and shape C defines the rotation angle of the valve member thus formed.

In a third step S3 section C* is pivoted towards section B*, around pivot axis D', such that there is no material outside the rotation, and the cylinder surfaces of notional body B smoothly transfers into cylinder surface of notional body C via a further notional body D coinciding with sphere segments E' and E" forming a pivot part D. The valve member 120 can now rotate between the two positions B* and C* over rotation angle alfa. By shaping a pivot part D in sphere form a rotation axis is defined. Pivot part D forms a transition area between the two angled cylinder forms B and C so that the valve member has a sealing edge with an edge face 115-3 proximal to the pivot points that coincide with a notional sphere body D formed by pivoting the intersection curve B* towards C*. In this way, the segments E' and E" deviate from the cylindrical forms of notional bodies B and C, so that the valve can smoothly pivot without a gap inside the tube inner wall or with only a very small gap smaller than a human egg cell. To further prevent seminal fluid or other watery fluids to enter the gap between valve member and inner tube wall, these or parts thereof may be formed by a hydrophobic material.

In fourth step S4, the valve member 120 is completed by cutting out inner cylinder F, collinear with cylinder body B, with a diameter d2. B', B", C' and C" are still cylinder surfaces, E' and E" are still sphere segments.

Figure 3:
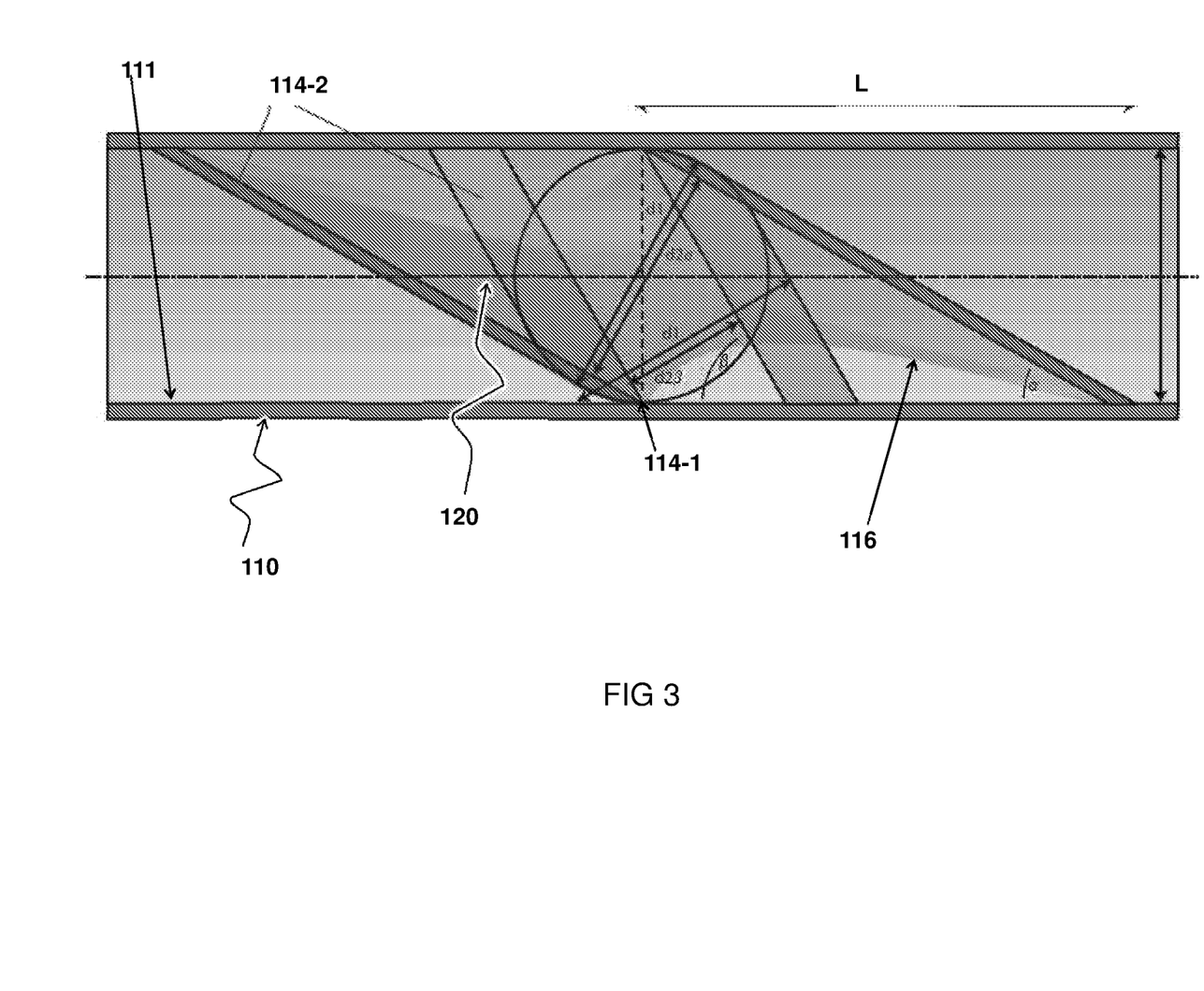
FIG. 3 shows in more detail the embodiment of FIG. 2.

FIG. 3 shows in more detail in the depicted embodiment that the sealing edge 116 of the valve member has a beak form with a length of beak that is also determined by a designated rotation angle. A change of shape of the beak thus depends on varying an inner diameter d2 of the valve member. A first diameter d2(alfa) is shown as a diameter of inner face part of the valve member. A second—smaller-diameter d2(beta) is shown as a diameter of inner face part of a pivoted member with an angle of rotation beta larger than alfa. For forming a valve member that closes off passage through the implantable tube cylinder B's inner diameter d2 is minimally of d1*cos alfa. A length L of the beak along the inner tube wall 111 in closed position is given by d1/tg alfa+½(d1−d2)/sin alfa.

Figure 4:
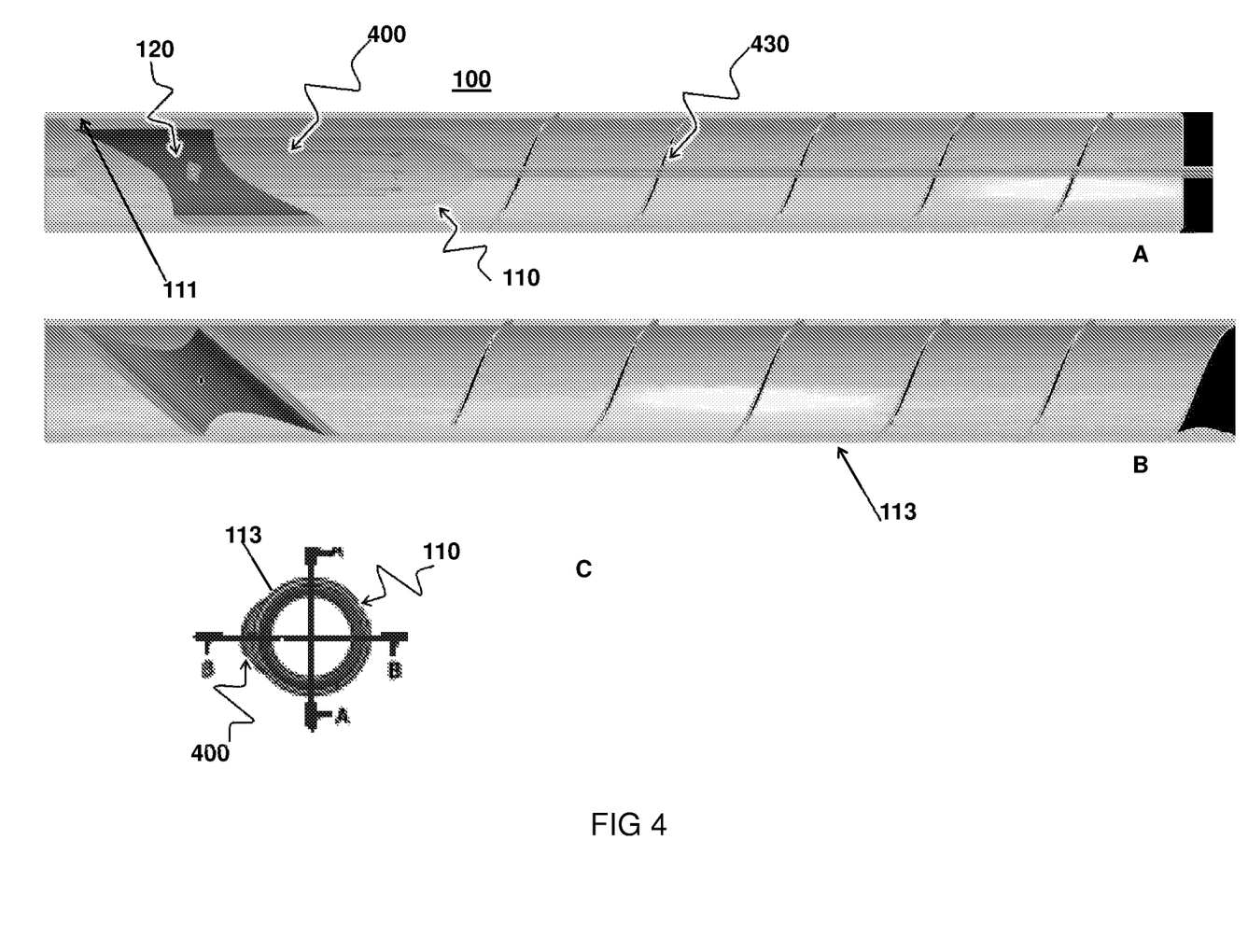
FIG. 4 shows another view of the implantable tube valve and actuator.

FIG. 4 shows an embodiment of the implantable tube valve 100 in open position (FIG. 4A) and closed position (FIG. 4B). Depending on the application, many types of actuators are possible for pivoting the valve member between open and closed positions. For example, the actuator may be a magnetostrictive, piezo or electromechanical actuator having well known actuator parts for pivoting the valve member. Also, depending on the application, the actuator can be of any suitable type, i.e. connected via wiring, together with an internal power source with or without a wireless actuation. Advantageously the implantable tube comprises an actuator 400, schematically illustrated in cross section in FIG. 4C. This actuator 400 can be applied in very minute geometries of less than 10×10 mm and can be even integrated inside the tube contour 113, so that the tube 110 is not or minimally deformed and suitable for insertion in the vessel, e.g. so that the tissue can stretch or accommodate to the protrusion.

Figure 5A:
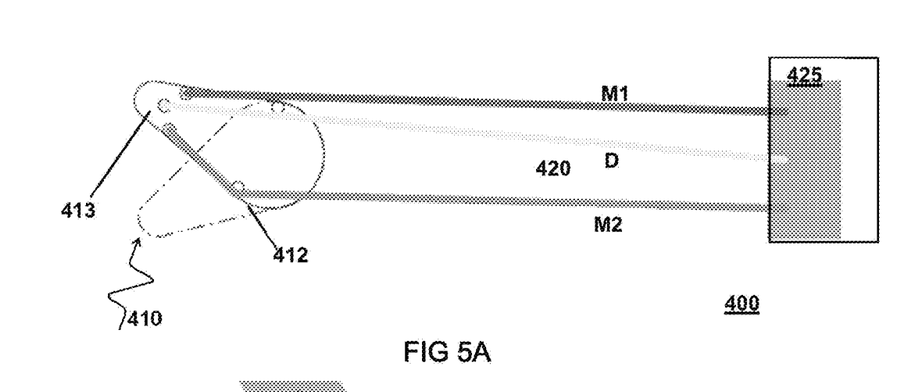
FIG. 5 shows detailed views on the actuator mechanism.
Figure 5B:
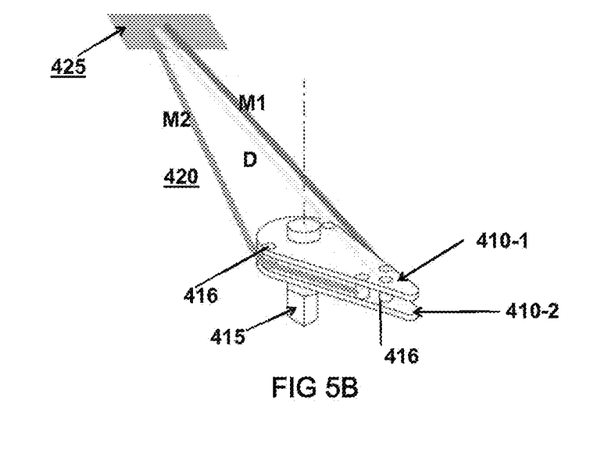

FIGS. 5A and 5B show detailed views on the actuator mechanism. Tension wires arrangement 420, when heated over a certain length may result in substantial contraction of the tension wires, resulting in a opening or closing the valve 120. The tension wires arrangement 420 is especially advantageous in the context of the present disclosure, but can also be used to good purpose in other actuators, notably of a type having an elongated geometry such as a tubes, cylinders or bars. In the illustrated embodiment, the actuator 400 comprises a cam 410 connected to the valve member 120 extending eccentrically from a rotation axis defined by the shaft mount 415; a heating circuit 425; and first and second tension wires M1, M2 formed of a shape metal alloy, connected to the heating circuit 425 and guided on opposite sides of the cam lever 410 along the tube wall, thereby connecting the cam 410 to a position fixed relative to the tube 110, so that, in use, the valve member 120 is pivoted in open position by heating the first tension wire M1 and the valve member is pivoted in closed position by heating the second tension wire M2. A number of variations are possible, e.g. by inverting the wire geometry and using push instead of pulling arrangements of the tension wires. Preferably, the tension wires M1, M2 are of a form, that contracts when heated. Shape metal alloy suitable for such may for instance a NiSn alloy known Nitinol, but other shape metal alloys can be used to purpose.

In the depicted embodiment the cam 410 is preferentially designed as a separate part on the outside of the implantable tube 100, leading to only a very minute extension of the external tube wall 113 in lateral direction. By extending the cam shape in lateral direction relative to the eccentric part, guides or off centric connectors 412 are formed on opposite sides.

Heating circuit 425 is preferably geared to a wireless charging device (not shown) but may also be powered by other means, e.g. a battery pack etc. In the shown embodiment the heating circuit comprises a charging capacitor (not shown) electrically connected to a charging antenna 430 arranged along the implantable tube. The heating circuit 425 comprises corresponding logic to heat a first or second tension wire M1, M2 when the charging capacitor is charged with a threshold charge, charged by the charging antenna 430. The logic may have further gearing options, e.g. a (wireless) read out, such as status check options or reset options, and is preferably operated by a coded signal that only activates the heating circuit 425 when a corresponding security code is transmitted. In its simplest form, the wireless charging system functions as a bistate switch, switching the valve member 120 from open to close position or from close to open, depending on the initial arrangement. Importantly but not necessarily the actuator is arranged with further (third) central tension wire D having a detent function. The central detent wire is elastic and connected to the cam, but not necessarily of a heat contractible type. For instance, it can be of a stainless steel material, or any material of suitable elasticity, ohmic resistance and thermal expansion coefficient. Similarly the detent wire D connects the cam to a position fixed relative to the tube. The detent is connected to the cam extension thereby bistably tensioning the cam in open or closed positions against a contraction force of first or second tension wires. Other types of bistable arrangements may be possible, with tensioning means, e.g. a spring or shaft arrangement with an eccentric e.g. polygonal cross-section. Furthermore, as shown in FIG. 5B, to guide the tension wires M1, M2 the cam has a layered construction with spacer guides 416. The central shaft 415 terminates at the bottom plate. The detent wire moves between upper and lower cam plates 410-1, 410-2 that is separated spacer guides 416. This improves the structural strength of the cam 410, and prevents possible cam deformation by tension of the detent wire D.

Figure 6:
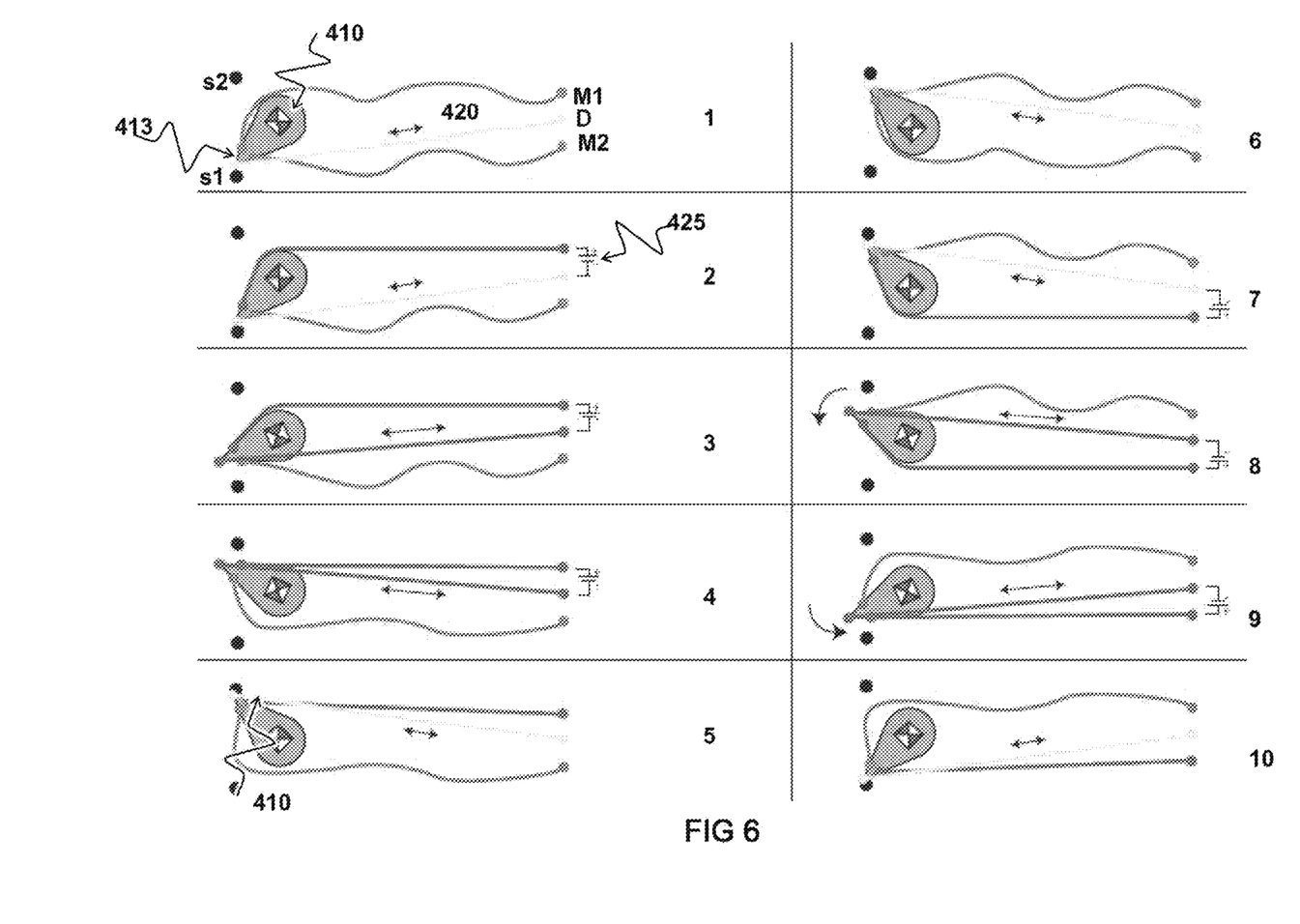
FIG. 6 showing states between back and forth rotation of the actuator.

The working of the actuator will be addressed in detail in subsequent FIG. 6 showing states S1-S10 between back and forth rotation of the actuator. Preferably, all tension wires 425 are connected to the cam 410 by a single electrical and mechanical connection 413, for example, by the cam being electrically conductive e.g. formed with a metal coating.

State 1 depicts a starting position, wherein the cam 410 is stably tensioned, by detent wire D against a lower stop S1, e.g. a stop corresponding with a closed position of the valve, i.e. the stop formed with the beak in closed position pressed against the inner tube wall. In this position, the heating circuit 425 is off—no tension is present in first and second memory metal wires M1, M2 and the valve member can be held closed without user power by keeping the cam lever 41—against the closed stop S1 by means of the detent wire D.

State 2 depicts actuation of the cam 410 by heating the first tension wire M1. The cam 413, with fixed connection to the valve member is pivoted in open position by heating the first memory metal wire M1 by current flowing through first memory metal wire M1 conductive cam 410 and detent wire D. The first tension wire M1 shortens due to heating of the memory shape alloy, thereby counteracting the tensioned detent wire D.

State 3 depicts a pivoting movement of the cam 410 as a result of the counteracting force exerted by the first tension wire M1 on the cam 410. Thereby the cam 410 rotates, and while heating the first tension wire M1, it shortens further, still against the tensioning force of the detent wire D, which is elastically stretched.

State 4 shows a pivoting point where the detent wire D passes a central line formed by the axis of rotation and the cam connection 413. Further rotation of the cam lever 410 results, due to the elastic pulling of detent wire D, in the cam being accelerated towards the second stop s2. The detent wire D is slightly longer (more stretched) in the middle position, so the two stable positions come from the wire being allowed to shorten (less stretched).

State 5 show the second bistable position, wherein the cam rotation is ended by the cam 410 being pulled by detent wire D under mild tension in position against the second stop s2 corresponding to an open position of the valve member.

State 6, going forward shows the cam 410 held fixed against the second stop s2 in off-status of the electric circuit. Similar to the first State 1, first and second tension wires M1, M2 are, since they are not heated, in untensioned condition.

State 7 starts the reverse of the condition depicted in State 2. Here the heating circuit 425 causes current to flow through detent wire D and second tension wire M2, connected on the electrically conductive cam 410, causing the second tension wire M2 to contract.

State 8 shows the cam 410 pivoting, against the tensioning force of the detent wire D, towards the first stop s1 by further contraction of the second tension wire M2.

State 9 shows the cam 410 still pivoting further, accelerated now both by second tension wire M2 and the detent wire D that passed the central line, resulting in State 10, which corresponds to the first State.

Further Embodiments

Figure 7:
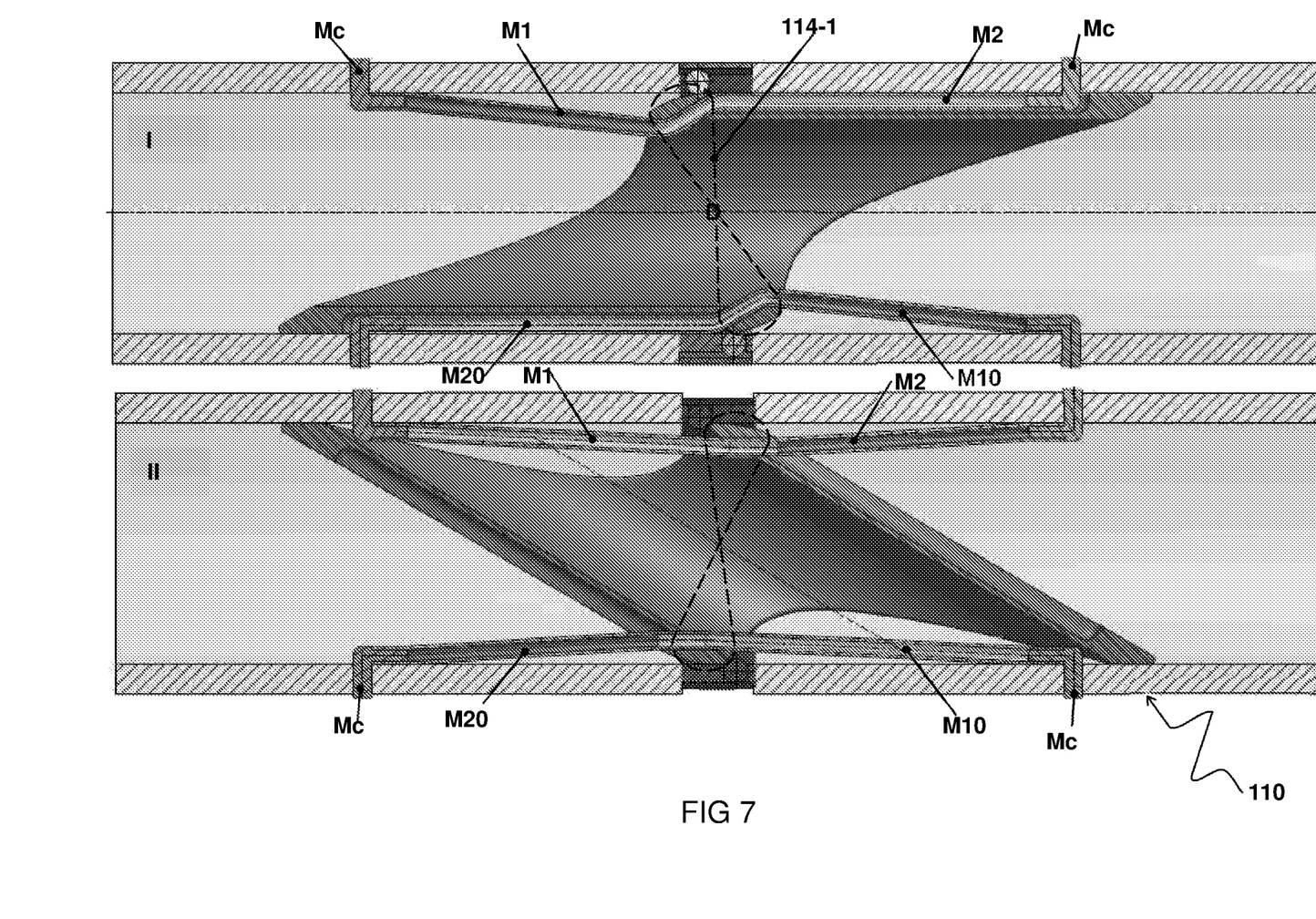
FIG. 7 shows an alternative embodiment of the implantable valve tube.

FIG. 7 shows an alternative embodiment of an implantable tube valve with an actuator embodiment that has wires directly attached to the valve member 120, so that parts of the valve member serve as a cam with connection parts for connecting the tension wires, to have the valve member 120 pivoting with shaft mount 415. In the embodiment, the actuator is formed by tubular mounting structure 110. The valve 120, functioning as actuating member is pivotable over pivot part D delineated by 114-2 relative to the mounting structure 110. A heating circuit (not shown) is designed in such a way that tension wires M1, M10, M2, M20 can be heated so that, in use, the actuating member is pivoted in a first position (I) by heating the first tension wires M1, M10 and the actuating member is pivoted in a second position (II) by heating second tension wires M2, M20. The embodiment provides a semi-one dimensional or planar structure for the actuator that offers the advantage of planar or semi-one dimensional design in a situation where there design space in one or two dimensions is limited. This can be achieved by eccentrically engaging tension wires on the actuating member 120. In the embodiment the tension wires connect to eccentric parts of and aligning them along the housing in single direction along the axis of elongation, notably, the tube axis. The term semi-one dimensional refers to design dimensions where the design space in directions transverse to the axis of elongation is very limited, at least in one direction. The tension wires are connected to the heating circuit external of the tube through via connections Mc.

The arrangements depicted in the embodiments are formed by three major constituents, notably, a valve member, actuator arrangement and powering device. These elements may be combined to benefit to provide the tiny dimensions of an implantable tube, but may be used separately for other applications, notably, valve arrangements that provide larger passage through the implantable tube where the actuator may be formed by other means. Also, the embodiments were directed to idealized shapes, but in practice may be suitably (de) formed e.g. in round, not necessarily circular forms and rotation symmetric, not necessarily spheric shapes but aspheric shapes for example, ellipsoid shapes. Further aspects of the invention are formed by an implantable tube as described in the above wherein the mount is formed by opposite shaft members protruding from the valve member through the tube wall thereby forming an axis of rotation. The heating circuit may be geared to a wireless charging device, the heating circuit electrically connected to a charging capacitor and a charging antenna arranged along the implantable tube; and wherein the heating circuit comprises logic to heat a first or second tension wire when the charging capacitor is charged with a threshold charge, charged by the charging antenna.

The invention claimed is:

1. An implantable tube valve configured to be implanted in a fallopian tube or urinary duct, the implantable tube valve comprising:
    an implantable tube having an inner tube wall forming a passage extending between two axial tube ends of the implantable tube;
    a valve member mounted inside the implantable tube and configured to pivot, using an actuator, between an open position and a closed position;
    wherein the valve member has an inner diameter of at least 2 mm so that the valve member has a size adapted for use in a fallopian tube or urinary duct and comprises:
    a sealing edge configured to contact the inner tube wall when the valve member is pivoted in the closed position for closing off passage through the implantable tube;
    an outer face that extends along a beak part and a pivot part of the valve member and extends from the sealing edge conformal to the inner tube wall of the implantable tube;
    an inner face that extends from the sealing edge conformal to the outer face for providing unobstructed passage through the implantable tube when the valve member is pivoted in the open position;
    wherein the implantable tube valve is configured such that, during use, the valve member smoothly pivots inside the inner tube wall of the implantable tube without a gap between the outer face of the valve member and the inner tube wall when the valve member is pivoted in the open position.

2. The implantable tube valve according to claim 1, wherein the actuator comprises:
    a pivotable cam connected to the valve member;
    a heating circuit;
    a first tension wire and
    a second tension wire
    wherein the first tension wire and the second tension wire are:
        aligned along the implantable tube,
        formed of a shape metal alloy,
        connected to the heating circuit, and
        eccentrically engaging the pivotable cam, and
        thereby enabling pivoting the pivotable cam to positions relative to the implantable tube, so that, in use, the valve member is pivoted to the open position by heating the first tension wire and the valve member is pivoted to the closed position by heating the second tension wire.

3. The implantable tube valve according to claim 2, further comprising a third tension wire, the third tension wire connecting the pivotable cam to a position fixed relative to the implantable tube, and
    wherein the third tension wire bistably tensions the pivotable cam in an open position and a closed position against a contraction force of one of the first tension wire and the second tension wire.

4. The implantable tube valve according to claim 3, wherein the third tension wire is part of the heating circuit, and wherein the third tension wire is not formed of a shape metal alloy.

5. The implantable tube valve according to claim 3, wherein the first, second and third tension wires are connected to the pivotable cam by a single electrical and mechanical connection.

6. The implantable tube valve according to claim 2, wherein the first and second tension wires are heat contractible.

7. The implantable tube valve according to claim 2, wherein the pivotable cam comprises an upper cam plate and a lower cam plate, wherein the upper cam plate is separated from the lower cam plate by a spacer guide that guides the first and second tension wires.

8. The implantable tube valve according to claim 1, wherein the beak part is formed by an intersection curve of a first notional body and second notional body, the first notional body coinciding with the inner tube wall and the second notional body formed by pivoting the first notional body over the pivot part.

9. The implantable tube valve according to claim 8, wherein the pivot part comprises:
    a proximal edge face; and
    a third notional body formed by rotating the intersection curve proximal to a pivot axis,
    wherein the proximal edge face coincides with the third notional body.

10. The implantable tube valve according to claim 9 wherein the implantable tube has a cylindrical inner tube wall extending continuously between said two axial tube ends; and
    wherein the first notional body is a cylinder forming an intersection curve with the cylindrical inner tube wall when the valve member is in the closed position, and
    wherein the third notional body is a sphere.

11. The implantable tube valve according to claim 8, wherein the beak part comprises a distal edge face that is contiguous with the inner tube wall when the valve member is in the closed position.

12. The implantable tube valve according to claim 1, wherein the sealing edge is a first sealing edge and the valve member comprises a second sealing edge that is axially symmetric relative to the first sealing edge.

* * * * *